United States Patent [19]

Pearlman

[11] 4,134,208
[45] Jan. 16, 1979

[54] ADJUSTABLE POSITIONING MEANS FOR ORTHODONTIC BRACKETS

[76] Inventor: Lawrence Pearlman, 601 Washington St., Norwood, Mass. 02062

[21] Appl. No.: 725,367

[22] Filed: Sep. 22, 1976

[51] Int. Cl.² .............................................. A61C 7/00
[52] U.S. Cl. .................................................. 32/14 A
[58] Field of Search .............................. 32/2, 14 A, 66

[56] References Cited

U.S. PATENT DOCUMENTS

| | | | |
|---|---|---|---|
| 1,907,923 | 5/1933 | Willis | 32/14 A |
| 3,521,355 | 7/1970 | Pearlman | 32/2 |

*Primary Examiner*—Robert Peshock
*Attorney, Agent, or Firm*—Wolf, Greenfield & Sacks

[57] ABSTRACT

An orthodontic handle for use in association with an orthodontic bracket to correctly position the bracket on the labial surface of a tooth. The handle has a first means for supporting the bracket and carries second means for determining the position of the bracket on the tooth. The second means interlocks with the handle in a plurality of predetermined positions. Preferably the handle and bracket are integrally formed of plastic as are the first and second means.

13 Claims, 9 Drawing Figures

U.S. Patent    Jan. 16, 1979    Sheet 1 of 2    4,134,208
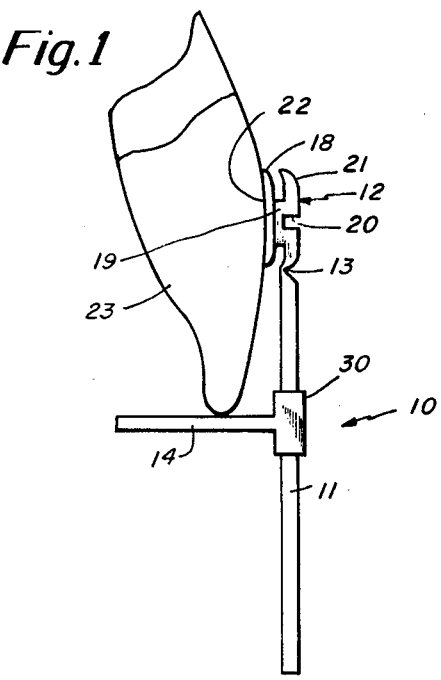
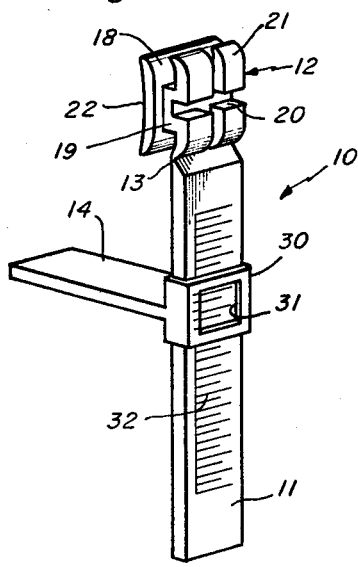
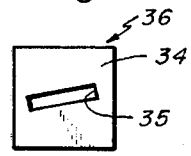
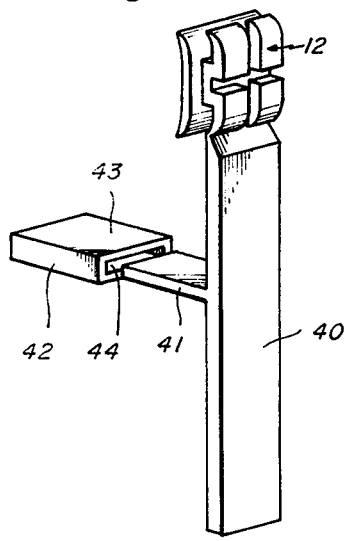
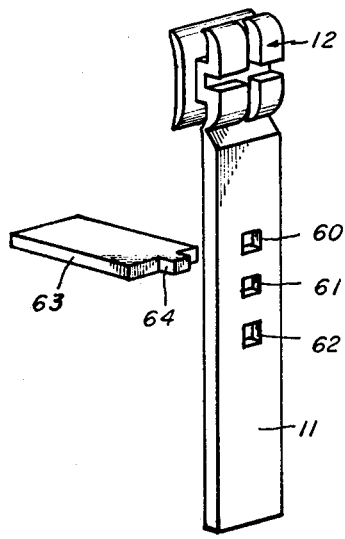
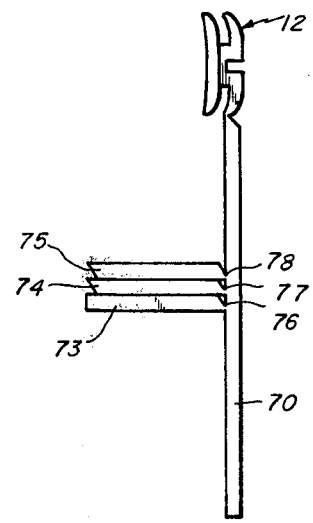
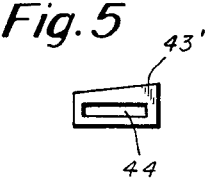

ADJUSTABLE POSITIONING MEANS FOR ORTHODONTIC BRACKETS

BACKGROUND OF THE INVENTION

It is now well-known in the orthodontic art to directly bond orthodontic brackets to teeth. Often such orthodontic brackets are plastic and may be as disclosed in U.S. Pat. No. 3,469,314.

U.S. Pat. No. 3,521,355 issued July 21, 1970 to the present inventor describes various positioning means and included an adjustable positioning means for positioning orthodontic brackets on teeth. It was recognized that it is important to be able to place orthodontic brackets simply and accurately on the labial surfaces of teeth as desired. It is equally important that in the cementing or bonding procedure the setting time or curing time of the adhesive used be undisturbed in order to prevent loss of effectiveness of this technique. It is therefore imperative to be able to not only handle the brackets effectively but also to be able to hold them precisely in place as needed during the setting time of the cement. If any movement occurs it affects the bonding of the bracket to the surface of the tooth by weakening the bond and eventually the bracket loosens and falls off. It is of primary significance to be able to handle and position the small brackets with accurate measurement and to bring them into and hold them in precise positions undisturbed during the cementing procedure.

Many brackets now on the market both of the plastic and metal type do not have supplementary means for simplifying the placement and cementing of such brackets accurately on teeth. In many cases, manufacturers recommend using various forms of hand-held tweezers which can be impractical and sometimes result in failures.

SUMMARY OF THE INVENTION

It is an object of this invention to provide an orthodontic handle for use in positioning orthodontic brackets on teeth with ease and with high accuracy although required positions may vary.

Still another object of this invention is to provide a handle in accordance with the preceding object which incorporates a positive measuring device that is adjustable providing for great versatility of the bracket and which can have provision for angulation of the bracket on the tooth.

It is another object of this invention to provide an improved adjustable handle in accordance with the preceding objects that can be used with ease so that personnel other than doctors can be trained to cement brackets using the handle of this invention.

Still another object of this invention is to provide an improved orthodontic handle in accordance with the preceding objects which can be formed integrally as a unit of plastic except at an adjustable interlock, and which has great strength and durability with a wide range of adjustment possible.

According to the invention an improved orthodontic handle for use in association with an orthodontic bracket to correctly position the bracket on the labial surface of the tooth has a first means for supporting an orthodontic bracket and carries second means for determining the position of the bracket on the tooth. The second means interlocks with the handle in a plurality of predetermined positions. Preferably the handle and bracket are integral and are formed of plastic as is the entire device.

Preferably a sliding arrangement is used in order to adjust the relationship of the bracket to the labial surface of the tooth. However, in some cases, peg arrangements and other adjusting means can be used. In all cases, the devices can be made at low cost and are easily used.

It is a feature of this invention that positive measuring is accomplished with ease and in highly compact and versatile devices. In many embodiments the bracket and handle are integrally formed yet they can be easily separated from each other. When metal and plastic are used high strength and durability can be provided in such structures. The correct angulation can be provided to a bracket by use of the handle of this invention while adjusting its up-down position on the tooth. Because of the ease of adjustment, both in angulation as well as up-down position, a minimized number of bracket and handle combinations can be used and stored which cover a wide range of measurements and tooth sizes with reduced storage and warehousing costs.

BRIEF DESCRIPTION OF THE DRAWINGS

The above and other features, objects and advantages of the present invention will be better understood from the following specification when read in conjunction with the accompanying drawings in which:

FIG. 1 is a side view of a preferred embodiment of this invention showing positioning on a tooth;

FIG. 2 is a perspective view thereof;

FIG. 3 is an end view of an attachment thereof;

FIG. 4 is a perspective view of an alternate embodiment of this invention;

FIG. 5 is an end view of an attachment thereof;

FIG. 6 is an exploded perspective view of still another embodiment thereof;

FIG. 7 is a side view of another embodiment thereof;

DESCRIPTION OF PREFERRED EMBODIMENTS

Figure 8:
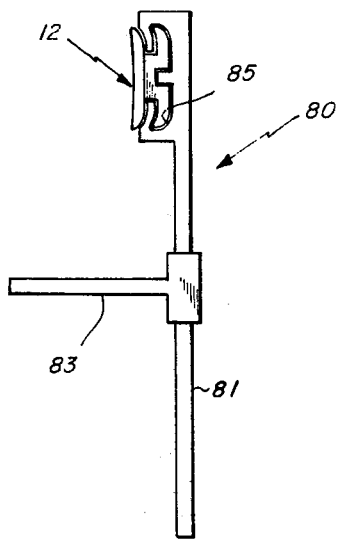
FIG. 8 is a perspective view of an alternate embodiment of a handle of this invention.

With reference now to FIGS. 1-3 a preferred embodiment 10 is illustrated comprising an elongated handle portion 11 integrally attached to an orthodontic bracket 12 at a frangible joint 13 with an adjustable gauge 14 which acts as a means interlocking with the handle portion 11 in a plurality of predetermined positions. The joint portion 13 acts as a means for supporting the orthodontic bracket 12.

The bracket 12 can be of conventional plastic design with a base 18, an upward extension 19 carrying a transverse groove 20 with upwardly and outwardly extending slightly overturned wings such as 21 for attachment of ligating wires. Such brackets are known in the art for use directly on individual teeth. The brackets can be attached by conventional adhesives to the teeth. Preferably the brackets have a curved rear surface 22 for attachment to the labial surface of a tooth such as 23 schematically shown in FIG. 1. While it is preferred that the brackets be integrally attached to the handle portions 11, in some cases, they can be separated or not integrally formed and later attached, and/or formed of other materials than the same plastic as the handles. The plastic of the integral attachments are preferably materials such as polystyrene, impact polystyrene, methylmethacrylate, polycarbonates or the like. A polycarbonate, such as Lexan, is particularly preferred because it is resistant to normal conditions found in the mouth of the user.

The gauge or shelf portion 14 preferably extends at a right angle from the handle portion 11 and as best shown in FIG. 1 has an encircling slider collar portion 30 which tightly fits the handle portion 11 so as to slide axially thereon in frictional engagement. Preferably a cutout 31 is provided in a face wall of the slider portion 30 and millimeter and half millimeter markings are formed on a scale 32 axially arranged along the handle portion 11. Thus, one can determine with preciseness the particular millimeter marking which one wishes to use for the shelf 14. Thus as shown in FIG. 1, the gauge 14 can be adjusted to touch the bottom of the tooth when the bracket is in its correct position. Thereafter, that marking forms a predetermined position and additional brackets can be placed on other teeth with regard to the dimensions used for the first tooth.

While the shelf 14 is often horizontal as shown in FIG. 2, an additional slider as suggested in FIG. 3 can be used. The slider 36 is a generally rectangular block 34 of plastic having a cutout 35 askew to the top surface 36 of the slider. The slider mounts with the cutout 35 tightly engaging member 14 so as to provide top flat surface 36 at an angle to the bottom surface of the tooth. This allows angulation of the bracket as desired. Of course the angle of the cutout 35 to the top surface 36 determines the angle of placement.

In other embodiments which enable angulation, the shelf 14 can itself have a top surface which is not horizontal or parallel to the bracket ligating wire notch but is askew thereto. Thus the top surface of shelf 14 may provide required angulation.

While the cutout for sliding in both the block 36 and the slide portion 30 are generally rectangular, any particular cross sectional shape can be used so long as a tight frictional sliding arrangement is used.

In a variation of the embodiment of FIG. 1 as best shown in FIG. 6, the slide section 30 is replaced by a series of square notches 60, 61 and 62 placed at predetermined distances along the axial length of the handle portion 11. The shelf or gauge 63 provides a square peg 64 which can be attached by a frictional fit to any of the notches 60, 61, 62 to provide a predetermined positioning between the bottom surface of the tooth which rests on the shelf and the bracket. A slider such as 34 can be used with the shelf 63 if desired.

In still another embodiment of the invention as best shown in FIG. 7, an integral, plastic, rectangular elongated handle portion 70 has a bracket 12 integrally attached thereto and formed of the same plastic with breakaway shelves 73, 74, 75 attached to the handle at points 76, 77 and 78 along thin lines of attachment which are frangible. Each of these shelves can be broken away by the hand to change the distance from the top-mostsurface to the bottom of the tooth as may be desired.

In still another embodiment of this invention as best illustrated in FIGS. 4 and 5, the bracket 12 of plastic is integrally molded with the elongated rectangular handle 40 which has a perpendicular permanently positioned shelf 41 extending therefrom. Shelf 41 is at a right angle to the handle 40 and carries a slider 42, with a top surface 43 which rests against the bottom of the tooth. The slider 42 has a cutout 44 so that it can be mounted in sliding, frictional engagement with the shelf 41.

The thickness of the slider 42 determines the position of the bracket with respect to the bottom of the tooth. Different thickness sliders can be used to vary the distance. In addition as shown in FIG. 5, a top surface 43' can be provided at an angle to the cutout 44 in order to provide for angulation. Sliders such as 34 and 42 can be interchanged in the various embodiments of this invention as will be obvious to those skilled in the art.

Figure 9:
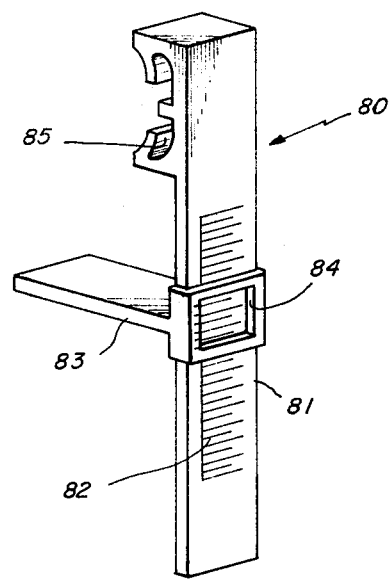
FIG. 9 is a side view thereof showing an attached bracket to be positioned by the handle of this invention.

FIGS. 8 and 9 illustrate still another embodiment of this invention wherein the handle portion 81 of a handle 80 has a scale 82 as previously described with a slider 83 providing a shelf substantially identical to shelf 14 previously described having the cutout portion 84 to view the scale 82. There is a tight friction slip fit between the components so as to provide for any desired positioning of the shelf portion 83. The scale can be carried on the shelf portion collar and a pointer provided on the handle portion 81 in an obvious reversal of parts. The embodiment 80 differs from the other embodiments of this invention previously described in that a bracket carrying means is formed as an integral part of the handle and allows attachment and detachment of a bracket as desired. This means is illustrated at 85 in the form of a cutout which is adapted to slidably receive a bracket as best illustrated in FIG. 9. The bracket 12 can be any conventional bracket as previously described. Thus it can be formed of plastic or metal as desired. In some cases the handle itself can be formed partly or wholly of metal. This embodiment provides a reusable, sterilizable delivery system. The bracket is slid into the bracket receiving cutout and held in the undercut portion of the bracket. Adhesive can then be applied to the bracket and the bracket can be applied to the tooth using the shelf as a measuring means. After positioning, the handle is merely drawn to the side to remove it from the tooth. Of course the shelf 83 can be provided with sliders such as 43 and 34 previously described.

While specific embodiments of the present invention have been shown and described, many variations are possible as will be apparent to those skilled in the art.

What is claimed is:

1. An orthodontic handle for use in association with an orthodontic bracket to correctly position said bracket on the labial surface of a tooth,
    said handle having a first means for supporting an orthodontic bracket and carrying second means for determining the position of said bracket on said tooth, said second means interlocking with said handle in a plurality of predetermined positions,
    said second means comprising an enclosing collar mounting a positioning shelf with said collar being slidably mounted on said handle in frictional engagement therewith,
    means for changing the angular relationship of a surface of said shelf with respect to a tooth against which said handle is positioned.

2. An orthodontic handle in accordance with claim 1 wherein said means comprises a sliding block providing an angularly arranged top surface.

3. An orthodontic handle for use in association with an orthodontic bracket to correctly position said bracket on the labial surface of a tooth,
    said handle having a first means for supporting an orthodontic bracket and carrying second means for determining the position of said bracket on said tooth, said second means interlocking with said handle in a plurality of predetermined positions, said second means comprising a plurality of peg and cutout arrangements to enable mounting of a positioning shelf at varying positions on said handle.

4. An orthodontic handle for use in association with an orthodontic bracket to correctly position said bracket on the labial surface of a tooth, said handle having a first means for supporting an orthodontic bracket and carrying second means for determining the position of said bracket on said tooth, said second means interlocking with said handle in a plurality of predetermined positions, said orthodontic bracket being formed of a plastic integral with said handle and further carrying a plurality of integral, parallel shelves frangibly mounted on said handle whereby one or more of said shelves may be removed to vary the position of said second means with respect to said bracket.

5. An orthodontic handle for use in mounting an orthodontic bracket to correctly position said bracket on the labial surface of the tooth, said handle and bracket being integrally formed of a plastic material, said handle comprising a handle portion having an outwardly extending positioning shelf, said shelf mount being substantially perpendicular to said handle portion, means for positioning on said shelf to predetermine the position of said bracket with respect to said shelf, said means comprising a block providing a top surface spaced a predetermined distance above said shelf and at a predetermined angle to said shelf to provide for desired angulation of said bracket with respect to a tooth.

6. An orthodontic handle in accordance with claim 5 and further comprising said block having a top surface parallel to a top surface of said shelf.

7. An orthodontic handle in accordance with claim 5 and further comprising said shelf having a top surface at an angle other than 90° to a plane through a top surface of said shelf.

8. An orthodontic handle for use in association with an orthodontic bracket to correctly position said bracket on the labial surface of a tooth, said handle having a first means for supporting an orthodontic bracket and carrying second means for determining the position of said bracket on said tooth, said second means interlocking with said handle in a plurality of predetermined positions, said second means comprising an enclosing collar mounting a positioning shelf with said collar being slidably mounted on said handle in frictional engagement therewith, said handle having an undercut bracket gripping portion at the upper end thereof, said bracket gripping portion gripping a bracket in sliding frictional engagement therewith whereby said bracket may be positioned on a tooth and adhered thereto with the handle slidably removed from the bracket thereafter.

9. An orthodontic handle for use in association with an orthodontic bracket to correctly position said bracket on the labial surface of a tooth, said handle having a first means for supporting an orthodontic bracket and carrying second means for determining the position of said bracket on said tooth, said second means interlocking with said handle in a plurality of predetermined positions, said second means comprising an enclosing collar a positioning shelf with said collar being slidably mounted on said handle in frictional engagement therewith, said second means further comprises a shelf, a plurality of sliding blocks adapted to frictionally engage said shelf, each of said blocks being of a different height whereby a selected one of said blocks can be used to determine the positions of said bracket.

10. An orthodontic handle for use in association with an orthodontic bracket to correctly position said bracket on the labial surface of a tooth, said handle having a first means for supporting an orthodontic bracket and carrying second means for determining the position of said bracket on said tooth, said second means interlocking with said handle in a plurality of predetermined positions, said second means comprising a shelf integral with a handle portion, and a plurality of blocks arranged to slidably engage said shelf whereby a selected block can be used to predetermine theposition of said bracket with respect to a tooth with which the handle is used.

11. An orthodontic handle for use in association with an orthodontic bracket to provide a delivery system for accurately positioning brackets on the labial surface of teeth, said handle having an undercut bracket gripping portion at an upper end thereof, said bracket gripping portion having means for slidably engaging a bracket to position said bracket on a tooth where the bracket is adhered and the handle slidably removed from the bracket, a positioning means for determining the position of said bracket on said surface, said positioning means interlocking with the handle in a plurality of predetermined positions.

12. An orthodontic handle in accordance with claim 11 wherein said positioning means interlocks in a sliding friction joint.

13. An orthodontic handle in accordance with claim 12 wherein said positioning means comprises a shelf and a sliding block designed to underlie a tooth.

* * * * *